United States Patent
Seward et al.

(10) Patent No.: US 7,465,298 B2
(45) Date of Patent: Dec. 16, 2008

(54) METHODS AND SYSTEMS FOR DELIVERING LIQUID SUBSTANCES TO TISSUES SURROUNDING BODY LUMENS

(75) Inventors: Kirk Patrick Seward, Dublin, CA (US); Lynn Barr, Lafayette, CA (US); Judith Carol Wilber, Oakland, CA (US)

(73) Assignee: Mercator Medsystems, Inc., San Leandro, CA (US)

( * ) Notice: Subject to any disclaimer, the term of this patent is extended or adjusted under 35 U.S.C. 154(b) by 422 days.

(21) Appl. No.: 10/610,790

(22) Filed: Jun. 30, 2003

(65) Prior Publication Data

US 2004/0010309 A1    Jan. 15, 2004

Related U.S. Application Data

(60) Provisional application No. 60/392,819, filed on Jun. 28, 2002.

(51) Int. Cl.
*A61M 31/00* (2006.01)
(52) U.S. Cl. .................................................. 604/508
(58) Field of Classification Search ............... 604/500, 604/506–508; 623/23.71, 1.49, 1.45, 1.42, 623/1.19, 1.11, 1.39
See application file for complete search history.

(56) References Cited

U.S. PATENT DOCUMENTS

| | | | |
|---|---|---|---|
| 5,112,305 A | 5/1992 | Barath et al. | |
| 5,196,024 A | 3/1993 | Barath | |
| 5,354,279 A | 10/1994 | Hofling | |
| 5,538,504 A | 7/1996 | Linden et al. | |
| 5,645,564 A | 7/1997 | Northrup et al. | |
| 5,681,281 A | 10/1997 | Vigil et al. | |
| 5,693,029 A | 12/1997 | Leonhardt | |
| 5,722,989 A | 3/1998 | Fitch et al. | |
| 6,059,815 A | 5/2000 | Lee et al. | |
| 6,102,933 A | 8/2000 | Lee et al. | |
| 6,283,947 B1 | 9/2001 | Mirzaee | |
| 6,605,114 B1 * | 8/2003 | Yan et al. | 623/1.43 |
| 6,776,792 B1 * | 8/2004 | Yan et al. | 623/1.15 |
| 2002/0002349 A1 * | 1/2002 | Flaherty et al. | 604/164.11 |
| 2002/0077592 A1 * | 6/2002 | Barry | 604/96.01 |

OTHER PUBLICATIONS

Braun-Dullaeus et al., "Cell cycle progression: new therapeutic target for vascular proliferative disease." *Circulation*. 1998; 98(1):82-9.

(Continued)

*Primary Examiner*—Kevin C Sirmons
*Assistant Examiner*—Catherine N Witczak
(74) *Attorney, Agent, or Firm*—Townsend and Townsend and Crew

(57) ABSTRACT

Methods, systems, and apparatus for delivering drugs and other substances to extraluminal tissue surrounding a body lumen are described. Catheters are used to inject the drug or other substance intraluminally into tissue surrounding a stent or other luminal scaffold. The drug or other substance is injected in an amount sufficient to cause diffusion back through the tissue to the stent. An absorptive structure, reservoir, or the like, on the stent then absorbs excess drug as it passes from the luminal tissue. In this way, the stent is first loaded with drug. After time, as the stent becomes fully loaded and the tissue becomes depleted, drug will be begin to flow back from the stent into the surrounding luminal tissue.

7 Claims, 4 Drawing Sheets

OTHER PUBLICATIONS

Chan et al., "Update on Pharmacology for Restenosis," *Current Interventional Cardiology Reports*, 2001, 3: 149-155.

de Smet et al., [abstract] "Metalloproteinase Inhibition Reduces Constrictive Arterial Remodeling After Balloon Angioplasty: A Study in the Atherosclerotic Yucatan Micropig." *Circulation*, 2000, 101:2962-2967.

Farsak et al., "Detection of *Chlamydia pneumoniae* and *Helicobacter pylori* DNA in human atherosclerotic plaques by PCR." *J Clin Microbiol* 2000; 38(12):4408-11.

Fuchs et al., [abstract] "Anti-angiogenesis: A new potential strategy to inhibit restenosis". *Intl J Cardiovasc Intervent.* 2001; 4:3-6.

Gallo et al., "Inhibition of Intimal Thickening After Balloon Angioplasty in Porcine Coronary Arteries by Targeting Regulators of the Cell Cycle." *Circulation.* 1999;99:2164-2170.

Grayston, Thomas J., "Antibiotic Treatment of *Chlamydia pneumoniae* for secondary prevention of cardiovascular events." *Circulation.* 1998;97:1669-1670.

Herdeg et al., [abstract] "Local paclitaxel delivery for the prevention of restenosis: biological effects and efficacy in vivo." *J Am Coll Cardiol* Jun. 2000; 35(7):1969-76.

Ismail et al., [abstract] "The role of infection in atherosclerosis and coronary artery disease: a new therapeutic target." *Heart Dis.* 1999;1(4):233-40.

Kol et al., [abstract] "Chlamydial and human heat shock protein 60s activate human vascular endothelium, smooth muscle cells, and macrophages." *J Clin Invest.* 1999; 103:571-577.

Lowe et al., [abstract] "Coronary in-stent restenosis: Current status and future strategies." *J Am Coll Cardiol.* Jan. 16, 2002; 39(2):183-93.

Lundemose et al., [abstract] "*Chlamydia trachomatis* Mip-like protein has peptidyl-prolyl cis/trans isomerase activity that is inhibited by FK506 and rapamycin and is implicated in initiation of chlamydial infection." *Mol Microbial.* 1993; 7(5):777-83.

Muhlestein et al., "Infection with *Chlamydia pneumoniae* accelerates the development of atherosclerosis and treatment with azithromycin prevents it in a rabbit model," *Circulation.* 1998; 97:633-636.

Varenne, "Gene Therapy for Coronary Restenosis: A Promising Strategy for the New Millenium?" *Current Interventional Cardiology Reports*, 2000; 2: 309-315.

\* cited by examiner

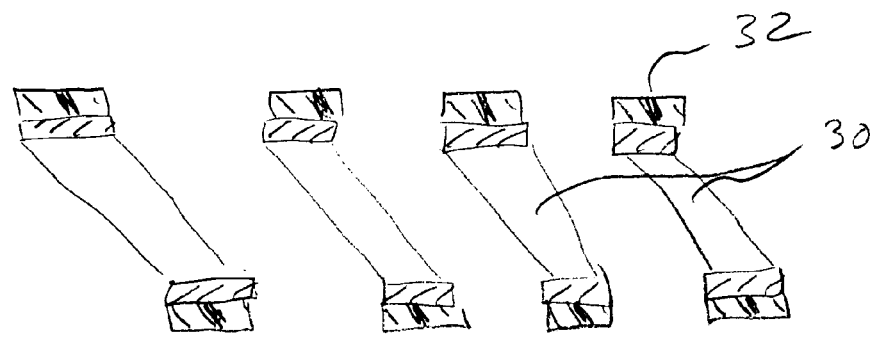
FIG_3
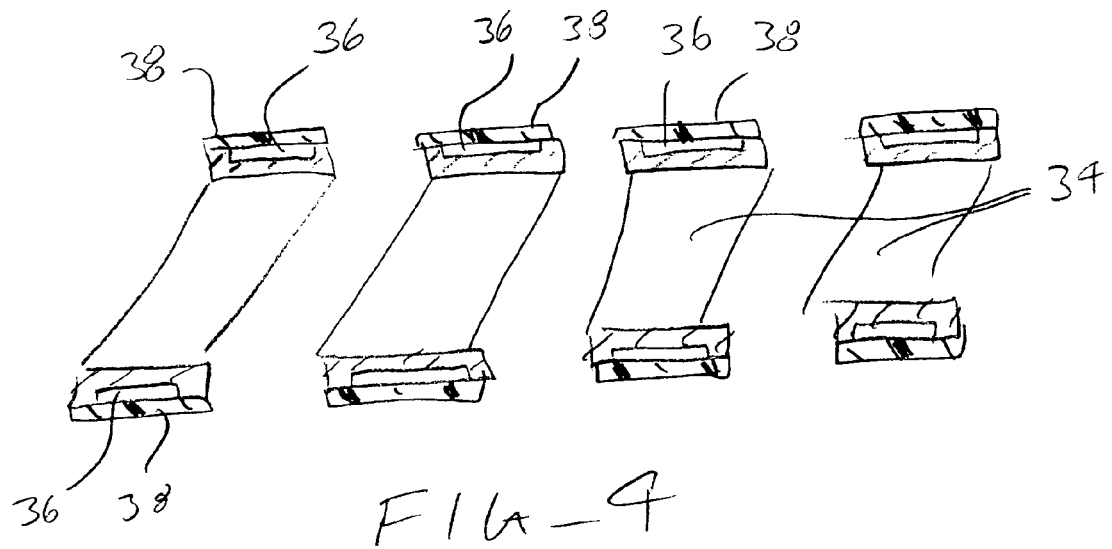
FIG_4

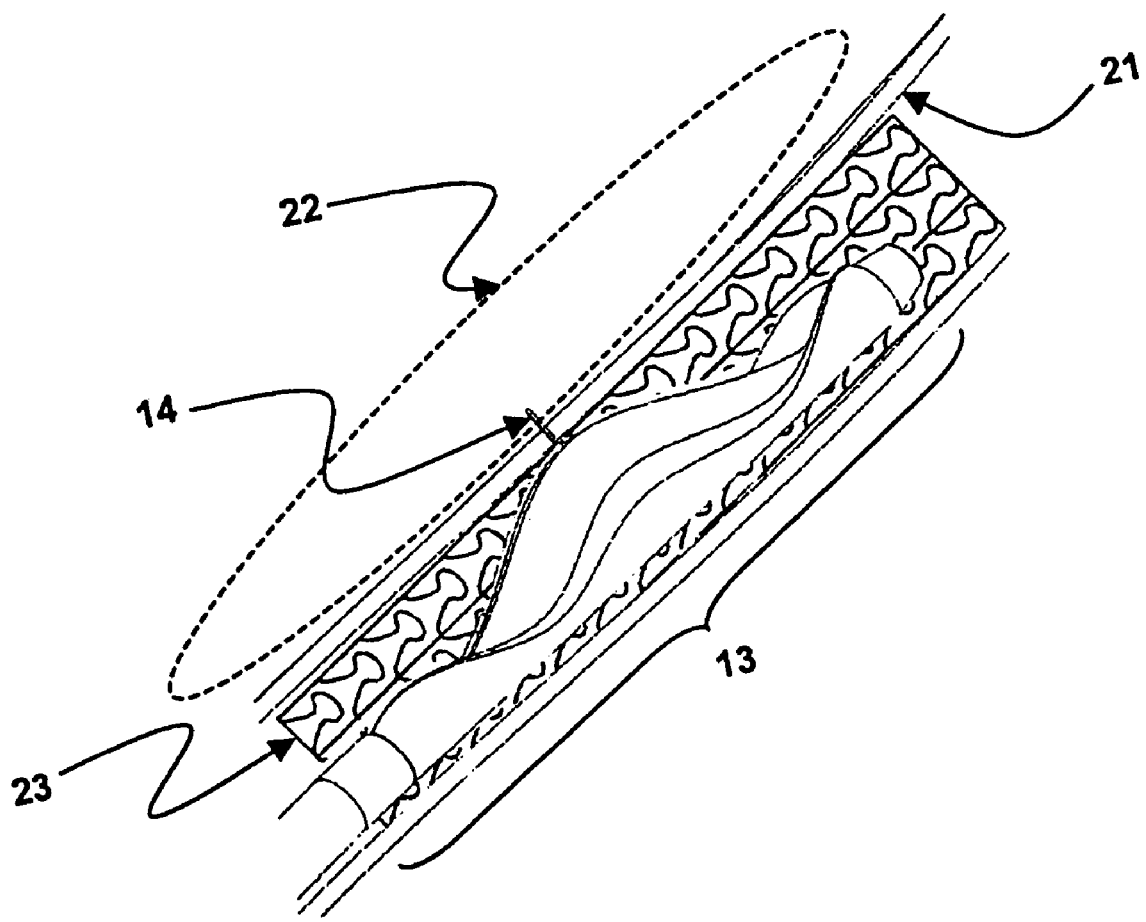
FIG_5

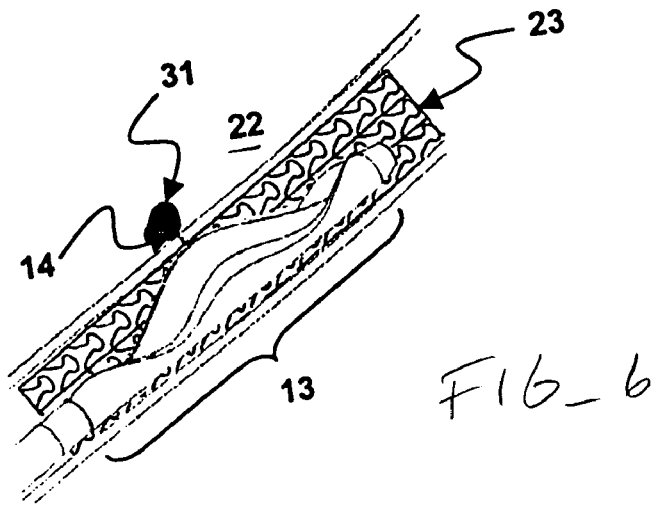
FIG_6
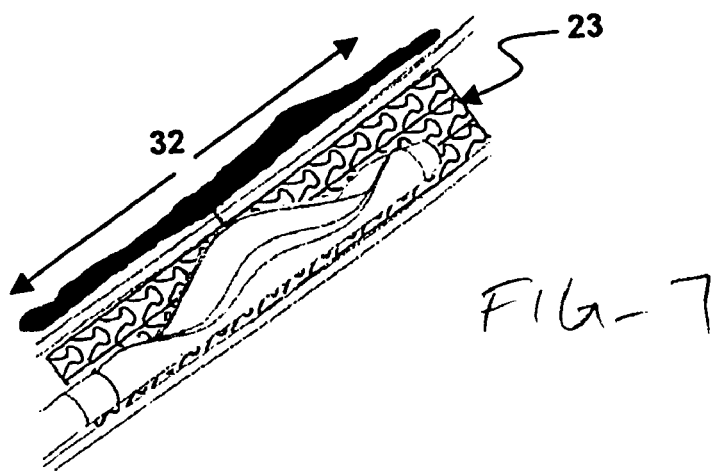
FIG_7
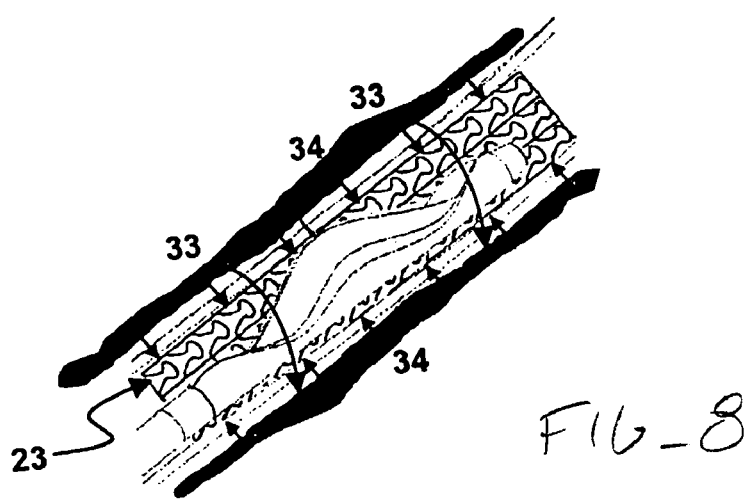
FIG_8

METHODS AND SYSTEMS FOR DELIVERING LIQUID SUBSTANCES TO TISSUES SURROUNDING BODY LUMENS

CROSS-REFERENCES TO RELATED APPLICATIONS

The present application is a non-provisional of U.S. patent application Ser. No. 60/392,819, filed Jun. 28, 2002, the full disclosure of which is incorporated herein by reference.

BACKGROUND OF THE INVENTION

1. Field of the Invention

The present invention relates generally to medical devices and methods. More particularly, the present invention relates to methods and systems for injecting liquid drugs into tissues surrounding body lumens, absorbing portions of the injected drugs as they pass out of the tissue at the luminal interface, and releasing the absorbed drugs back into the luminal tissue over time.

Coronary artery disease is the leading cause of death and morbidity in the United States and other western societies. In particular, atherosclerosis in the coronary arteries can cause myocardial infarction, commonly referred to as a heart attack, which can be immediately fatal or, even if survived, can cause damage to the heart which can incapacitate the patient.

While coronary artery bypass surgery is an effective treatment for stenosed arteries resulting from arthrosclerosis and other causes, it is a highly invasive procedure which is also expensive and which requires substantial hospital and recovery time. Percutaneous transluminal angioplasty (PTCA), commonly referred to as balloon angioplasty, is less invasive, less traumatic, and significantly less expensive than bypass surgery. Until recently, however, balloon angioplasty has not been considered to be as effective a treatment as bypass surgery. The effectiveness of balloon angioplasty, however, has improved significantly with the introduction of stenting which involves the placement of a scaffold structure within the artery which has been treated by balloon angioplasty. The stent inhibits abrupt reclosure of the artery and has some benefit in reducing subsequent restenosis resulting from hyperplasia.

Despite such improvement, patients who have undergone angioplasty procedures with subsequent stenting still suffer from a high incidence of restenosis resulting from hyperplasia. Very recently, however, experimental trials have demonstrated that the coating of stents with anti-proliferative drugs can significantly reduce the occurrence of hyperplasia, promising to make combined angioplasty and stenting a viable alternative to bypass surgery.

While holding great promise, the ability of drug-coated stents to inhibit hyperplasia is limited by the ability to bind effective amounts and concentrations of the drug onto the surface of the stent or other vascular prosthesis being used. In particular, the ability to load anti-hyperplastic drugs can be limited by the nature of the drug, the surface of the stent or other vascular prosthesis to which the drug is to be bound, or other causes.

In an effort to enhance the effectiveness of anti-hyperplastic drugs bound to stents, a common approach has been to entrap the drugs in a polymer matrix which is coated or otherwise disposed over the stent surface. While the use of such a polymer matrix may increase the amount of drug and/or provide for desired controlled release characteristics, such passive containment of the drug has a number of limitations.

As an alternative to using a polymer matrix, stents have also been provided with open reservoirs for holding drugs. Usually, the reservoirs will be covered by a porous membrane for maintaining the drug prior to use and releasing the drug in a controlled manner over time after the stent has been implanted.

Regardless of the particular approach chosen, drug-coated stents suffer from a number of shortcomings. In particular, the delivery and release of a drug from a stent will only provide drug at the luminal wall and not directly into the tissue surrounding the lumen. The amounts and concentrations of drugs carried by a stent is necessarily limited by the available surface area in the case of coated stents and the available stent volume in the case of stents having reservoirs. Moreover, delivering of the said drug at the luminal interface can be problematic since significant portions of the drug may be washed away, particularly in the case of drugs being delivered into blood vessels. Additionally, the delivery kinetics of the drug into the vascular or other luminal wall can be difficult to control and can require significant compromises in the design of the stent and the formulation of the drug being delivered.

As an alternative to stent-based luminal drug delivery, the direct injection of drugs into vascular and other luminal walls has recently been proposed. Of particular interest to the present invention, catheters carrying microneedles capable of delivering therapeutic and other agents deep into the adventitial layer surrounding blood vessel lumens have been described in co-pending application Ser. Nos. 09/961,080, filed on Sep. 20, 2001, and 09/961,079, also filed on Sep. 20, 2001, both applications having common inventorship with the present application. While the methods and apparatus described in these applications provide for highly advantageous luminal drug delivery, there are limitations associated with such injection protocols. First, injection requires the use of a catheter and can generally only be carried out once during an interventional procedure. Second, injected drugs, even those which are injected deep into the adventitia can be lost as they migrate to and through the luminal wall. Efforts to formulate injected drugs so that they have enhanced persistence in the tissue can require compromises with respect to other desirable drug characteristics.

For these reasons, it would be desirable to provide improved methods, systems, and apparatus for delivering drug to the tissues surrounding blood vessels and other body lumens. In particular, such improved methods and systems should overcome at least some of the deficiencies noted above with respect to drug delivery from stents and drug delivery via injection. More specifically, it would be desirable to combine beneficial aspects from each of the known delivery routes in order to provide for delivery of the drug into the adventitia with minimum loss of the drug in to the body lumen. At least some of these objectives will be met by the inventions described hereinbelow.

2. Description of the Background Art

The following references are pertinent to intravascular and intraluminal drug delivery.

O. Varenne and P. Sinnaeve, "Gene Therapy for Coronary Restenosis: A Promising Strategy for the New Millenium?" *Current Interventional Cardiology Reports*, 2000, 2: 309-315.

B. J. de Smet, et. al., "Metalloproteinase Inhibition Reduces Constrictive Arterial Remodeling After Balloon Angioplasty: A Study in the Atherosclerotic Yucatan Micropig." *Circulation*, 2000, 101: 2962-2967.

A. W. Chan et. al., "Update on Pharmacology for Restenosis," *Current Interventional Cardiology Reports*, 2001, 3: 149-155.

Braun-Dullaeus R C, Mann M J, Dzau V J. Cell cycle progression: new therapeutic target for vascular proliferative disease. *Circulation.* 1998; 98(1):82-9.

Gallo R, Padurean A, Jayaraman T, Marx S, Merce Roque M, Adelman S, Chesebro J, Fallon J, Fuster V, Marks A, Badimon J J. Inhibition of intimal thickening after balloon angioplasty in porcine coronary arteries by targeting regulators of the cell cycle. *Circulation.* 1999; 99:2164-2170

Herdeg C, Oberhoff M, Baumbach A, Blattner A, Axel D I, Schroder S, Heinle H, Karsch K R. Local paclitaxel delivery for the prevention of restenosis: biological effects and efficacy in vivo. *J Am Coll Cardiol* 2000 June; 35(7):1969-76.

Ismail A, Khosravi H, Olson H. The role of infection in atherosclerosis and coronary artery disease: a new therapeutic target. *Heart Dis.* 1999; 1(4):233-40.

Lowe H C, Oesterle S N, Khachigian L M. Coronary in-stent restenosis: Current status and future strategies. *J Am Coll Cardiol.* 2002 Jan. 16; 39(2):183-93.

Fuchs S, Komowski R, Leon M B, Epstein S E. Anti-angiogenesis: A new potential strategy to inhibit restenosis. *Intl J Cardiovasc Intervent.* 2001; 4:3-6.

Kol A, Bourcier T, Lichtman A H, and Libby P. Chlamydial and human heat shock protein 60s activate human vascular endothelium, smooth muscle cells, and macrophages. *J Clin Invest.* 103:571-577 (1999).

Farsak B, Vildirir A, Akyön Y, Pinar A, Öç M, Böke E, Kes S, and Tokgözoglu L. Detection of *Chlamydia pneumoniae* and *Helicobacter pylori* DNA in human atherosclerotic plaques by PCR. *J Clin Microbiol* 2000; 38(12):4408-11

Grayston J T. Antibiotic Treatment of *Chlamydia pneumoniae* for secondary prevention of cardiovascular events. *Circulation.* 1998; 97:1669-1670.

Lundemose A G, Kay J E, Pearce J H. *Chlamydia trachomatis* Mip-like protein has peptidyl-prolyl cis/trans isomerase activity that is inhibited by FK506 and rapamycin and is implicated in initiation of chlamydial infection. *Mol Microbiol.* 1993; 7(5):777-83.

Muhlestein J B, Anderson J L, Hammond E H, Zhao L, Trehan S, Schwobe E P, Carlquist J F. Infection with *Chlamydia pneumoniae* accelerates the development of atherosclerosis and treatment with azithromycin prevents it in a rabbit model. *Circulation.* 1998; 97:633-636.

K. P. Seward, P. A. Stupar and A. P. Pisano, "Microfabricated Surgical Device," U.S. application Ser. No. 09/877,653, filed Jun. 8, 2001.

K. P. Seward and A. P. Pisano, "A Method of Interventional Surgery," U.S. application Ser. No. 09/961,079, filed Sep. 20, 2001.

K. P. Seward and A. P. Pisano, "A Microfabricated Surgical Device for Interventional Procedures," U.S. application Ser. No. 09/961,080, filed Sep. 20, 2001.

BRIEF SUMMARY OF THE INVENTION

Methods, systems, and apparatus according to the present invention provide for injection of a liquid substance, typically a therapeutic substance as described in more detail below, into tissue surrounding a body lumen. The substances are injected into at least one location in the tissue, typically in the perivascular tissue surrounding a coronary or other artery, where the location is proximate a luminal scaffold which has been adapted to imbibe or absorb the substance as it migrates from the injection site back toward the body lumen. The imbibed substance is then released from the scaffold back into the tissue over time, thus reducing the amount of substance which is lost into the body lumen (and thereby increasing delivery efficiency) and extending the length of time during which effective levels of the drug can be maintained within the tissue.

The methods of the present invention may involve intraluminal injection of the substances at locations where the scaffold has previously been implanted, but such implantation is not necessarily a part of the methods of the present invention. Alternatively, implantation of the scaffold may be performed as part of the method of the present invention, either before substance injection, during substance injection, or subsequent to substance injection. It will be appreciated, of course, that the substance injection and/or the scaffold deployment may overlap completely, partially, or not at all.

While the methods, systems, and apparatus of the present invention will find their greatest use in intravascular applications, more particularly for delivery into arterial adventitia, and even more particularly for delivery into the adventitia surrounding the coronary arteries, they may also find use in non-vascular applications. For example, in applications where stenting is performed in other body lumens, such the ureter, urethra, biliary duct, and the like. In such cases, the combined drug and scaffold therapy may be particularly beneficial for the treatment of cancer and other conditions were neoplastic or other proliferative cell growth can close the body lumen.

The methods of the present invention may employ a wide variety of drugs or other substances. The substances must be formulated in an injectable form, usually being in liquid form, where the active substance may be dissolved in the liquid, dispersed in the liquid, or present in the liquid in any known pharmaceutical formulation which permits injection. The substances and/or carriers will usually be lipophilic, but may be hydrophilic, or combinations of lipophilic and hydrophilic. Exemplary agents to be incorporated in the substances of the present invention include antineoplastic agents, anti-proliferative agents, immunosuppressive agents, anti-inflammatory agents, macrolide antibiotics, antibiotics, antifungal, antivirals, antibodies, lipid lowering treatments, gene therapy agents, anti-sense drugs, metalloproteinase inhibitors, growth factor inhibitors, cell cycle inhibitors, angiogenesis drugs, anti-angiogenesis drugs, radio-opaque contrast media, and the like.

The scaffolds will usually be expandable, typically comprising an expandable frame component which may be in the form of a conventional vascular or other luminal stent. Such scaffolds and stents are typically composed of metals, such as stainless steel, shape memory alloys (such as nitinol), or the like. Usually, such expandable frames will be at least partly covered by a liquid absorptive structure, such as a hydrophilic polymer, a hydrophobic polymer, a porous ceramic, or phosphorylcholine layer, or the like. Phosphorylcholine coatings are available from BioCompatibles UK Ltd., Farnham, Surrey, United Kingdom.

As an alternative to using an absorptive structure, the scaffold may have a reservoir formed in the surface thereof. Suitable reservoirs include channels, divots, recesses, or the like, and will usually be covered by a porous membrane which provides for controlled release of the substance which is carried in the reservoir. In a further aspect of the present invention, systems for delivering such liquid substances into the perivascular or other tissue surrounding a body lumen comprise a catheter and a stent. The catheter will have an injection needle near a distal end thereof, and will be capable of injecting the liquid substance into the tissue, e.g., into the adventitial tissue surrounding an artery. The stent will have an absorptive structure or reservoir for holding the drug, the catheter may be used to inject the liquid into the tissue surrounding the body lumen and the stent may be implanted into the body lumen to absorb the injected liquid substance(s) as they migrate from the tissue toward the body lumen. The liquid substances absorbed by the stent will then be released back into the tissue over time.

The present invention still further comprises stents for use in absorbing substances injected into tissue surrounding a body lumen. Such stents comprise an expandable component and an absorptive structure disposed over at least a portion of the surface of the expandable component. The absorptive structure may have any of the forms described above in connection with the methods of the present invention.

BRIEF DESCRIPTION OF THE DRAWINGS

FIG. 3 illustrates a first embodiment of the stent useful in the methods of the present invention.

FIG. 4 illustrates a second embodiment of a stent useful in the methods of the present invention.

FIGS. 5-8 illustrate the method of the present invention for injecting a liquid substance into the adventitial region surrounding a blood vessel according to the present invention.

DETAILED DESCRIPTION OF THE INVENTION

Figure 1:
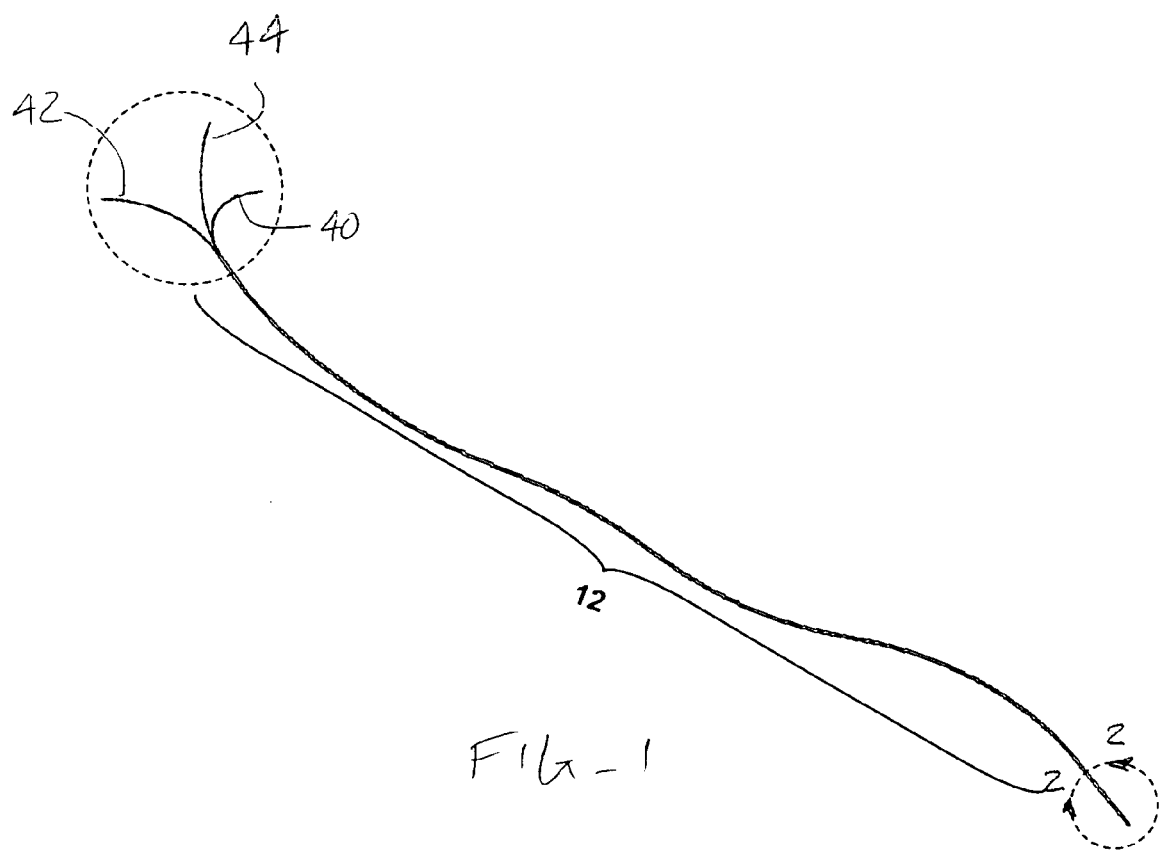
FIG. 1 illustrates an intravascular injection catheter suitable for use in the methods of the present invention.

The methods, systems, and apparatus of the present invention can be used to deliver a wide variety of therapeutic and other agents to extra luminal tissue surrounding body lumens, particularly the adventitial layer and other perivascular tissues surrounding arteries and blood vessels, particularly coronary arteries. These agents include antineoplastic agents, antiproliferative agents, immunosuppressive agents, anti-inflammatory agents, macrolide antibiotics, antibiotics, antifungals, antivirals, antibodies, lipid lowering treatments, gene therapy agents, anti-sense drugs, metalloproteinase inhibitors, growth factor inhibitors, cell cycle inhibitors, angiogenesis drugs, anti-angiogenesis drugs, and/or radioopaque contrast media for visualization of the injection under guided X-ray fluoroscopy. Each of these therapeutic agents has shown promise in the treatment of cardiovascular disease, restenosis, and/or vulnerable plaque lesions.

Antiproliferative agents, immunosuppressive agents, and anti-inflammatory agents, including but not limited to AVI-4126, sirolimus, tacrolimus, everolimus, cortisone, dexamethasone, and cyclosporine, interfere with the pathological proliferative response after coronary angioplasty to prevent intimal hyperplasia, smooth muscle cell activation and migration, and neointimal thickening.

Antineoplastic agents, including but not limited to paclitaxel and actinomycin D, interfere with the pathological proliferative response after coronary angioplasty to prevent intimal hyperplasia, smooth muscle cell activation and migration, and neointimal thickening.

Macrolide antibiotics, including but not limited to sirolimus, tacrolimus, everolimus, azithromycin, clarithromycin, and erythromycin, inhibit or kill microorganisms that may contribute to the inflammatory process that triggers or exacerbates restenosis and vulnerable plaque. In addition, many macrolide antibiotics, including but not limited to sirolimus and tacrolimus, have immunosuppressive effects that can prevent intimal hyperplasia, neointimal proliferation, and plaque rupture.

Antibiotics, including but not limited to sirolimus, tacrolimus, everolimus, azithromycin, clarithromycin, doxycycline, and erythromycin, inhibit or kill microorganisms that may contribute to the inflammatory process that triggers or exacerbates restenosis and vulnerable plaque.

Antifungals, including but not limited to sirolimus, everolimus, and tacrolimus, inhibit or kill microorganisms that may contribute to the inflammatory process that triggers or exacerbates restenosis and vulnerable plaque.

Antivirals, including but not limited to acyclovir, ganciclovir, fancyclovir and valacyclovir, inhibit or kill viruses that may contribute to the inflammatory process that triggers or exacerbates restenosis and vulnerable plaque.

Antibodies may be developed to inhibit or kill microorganisms that may contribute to the inflammatory process that triggers or exacerbates restenosis and vulnerable plaque or to inhibit specific growth factors or cell cycle regulators.

Lipid-lowering treatments, including but not limited to statins, modify plaques, reducing inflammation and stabilizing vulnerable plaques.

Gene therapy agents achieve overexpression of genes that may ameliorate the process of vascular occlusive disease or the blockade of the expression of the genes that are critical to the pathogenesis of vascular occlusive disease.

Anti-sense agents, including but not limited to AVI-4126, achieve blockade of genes and mRNA, including but not limited to c-myc, c-myb, PCNA, cdc2, cdk2, or cdk9s, through the use of short chains of nucleic acids known as antisense oligodeoxynucleotides.

Metalloproteinase inhibitors, including but not limited to batimastat, inhibit constrictive vessel remodeling.

Cell cycle inhibitors and modulators and growth factor inhibitors and modulators, including but not limited to modulators of VEGF, IGF, and tubulin, inhibit or modulate entry of vascular smooth muscle cells into the cell cycle, cell migration, expression of chemoattractants and adhesion molecules, extracellular matrix formation, and other factors that trigger neointimal hyperplasia.

Angiogenesis genes or agents increase microvasculature of the pericardium, vaso vasorum, and adventia to increase blood flow.

Anti-angiogenesis genes or agents inhibit factors that are associated with microvascularization of atherosclerotic plaque and which directly or indirectly also induce smooth muscle cell proliferation.

Figure 2:
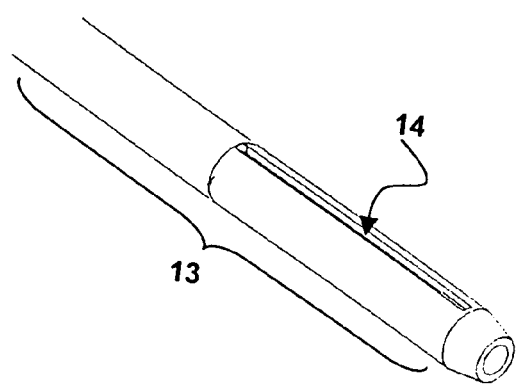
FIG. 2 is a detailed view of the distal end of the catheter of FIG. 1 taken along line 2-2.

Referring now to FIGS. 1, 2, and 5, a catheter 12 having a microneedle 14 suitable for injection of substances into luminal walls according to the methods of the present invention is illustrated. As shown in FIG. 2, the microneedle 14 is retracted within an involuted section of the catheter at its distal end 13. The mirconeedle 14 may be advanced in a radial direction so that it penetrates into a region 22 of extra vascular tissue through wall 21 of an artery, as best shown in FIG. 5. In particular, the portion of the catheter which carries the needle is inflated, as described in more detail in co-pending U.S. application Ser. Nos. 09/961,080, filed on Sep. 20, 2001, and 09/961,079, also filed on Sep. 20, 2001, incorporated herein by reference.

The systems of the present invention will further comprise stents, grafts, or other scaffold structures having absorbable structures, reservoirs, or the like, for imbibing liquid substances after they are injected into the luminal tissues. As shown in FIG. 3, the stent may comprise a helical scaffold 30, which may have any conventional helical stent structure, with an absorptive polymer layer 32, formed over at least part of its exterior surface. Polymer layer 32 will be porous or alternatively comprise a hydratable gel or similar material which is capable of imbibing the drug or other liquids substance which has been injected into the luminal wall as said substance is shed or expressed from the wall. In particular, the polymer material 32 will be able to absorb the liquid drug or other substance and then release the substance back into the luminal wall over time.

As shown in FIG. 4, a helical stent 34 has open reservoirs 36 formed over at least a portion of its exterior surface. The reservoirs 36 are covered with porous membranes 38 which permit entry of the liquid substance into the reservoir as the substance is released from the surrounding luminal wall (after the stent has been deployed in the target lumen). As with the absorptive material of FIG. 3, the liquid substance in the reservoirs 36 will first be collected within the reservoirs and subsequently released from the reservoirs back into the luminal wall over time.

Referring again now to FIG. 5, the catheter 12 will be deployed in the blood vessel and the microneedle 14 passed into the adventitial space 22 through openings in a stent 23. The stent 23 may have the structures of either FIGS. 3 or 4, or any other structure which has been modified to have the desired absorption capability of the present invention. The stents may be employed by conventional means, including balloon expansion, release of self-expanding stents from constraint, or combinations thereof.

After deployment of the stent 32, and penetration of the microneedle 14 into the target luminal tissue, the liquid substance will be delivered into the tissue through the microneedle, typically from a port 40 located at a proximal end of the catheter 12 (FIG. 1). Remaining ports 42 and 44 are available for expansion of the catheter in order to employ the microneedle, advance of a guidewire, or the like.

Initially, a small bolus of material is delivered so that it forms a small plume 31 (FIG. 6). Further injection of the material causes diffusion of the material both in a longitudinal direction 32 (FIG. 7) and eventually in a circumferential direction 34 (FIG. 8). After the tissue becomes saturated, excess liquid substance will diffuse back toward the lumen, eventually passing through the arterial or other luminal wall and into the absorptive structures or reservoirs of the stent 23. After the stent is loaded, and in particular after the concentration of the drug within the surrounding tissue lowers, the liquid substance will begin to flow back into the luminal tissue because of the growing concentration gradient. In this way, maintenance of a reservoir of the drug adjacent to the tissue will be maintained for relatively long periods of time to enhance treatment.

Desired drugs or other therapeutic agents can exist in particulate, nanoparticulate, liquid, suspended, or aqueous states. As the drug exits the delivery needle, the longitudinal length of diffusion will depend principally on the amount of drug injected and secondarily on the lipophilicity of the drug. In the case of vascular delivery, the dispersion will further depend on the nature of the vaso vasorum to transfer the drug into the different layers of the blood vessel wall and surrounding tissue. Similar factors will influence the rate of diffusion of the drug back into the stent absorptive structures and reservoirs of the present invention.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for delivering a liquid substance to tissue surrounding a blood vessel, said method comprising:
   injecting the substance into at least one location in the tissue by advancing an injection needle from a lumen of the blood vessel into the tissue; and
   implanting a luminal scaffold at said location after the substance has been injected, wherein the luminal scaffold is adapted to imbibe the substance released from the tissue after injection and to release the imbibed substance back into the tissue over time.

2. A method as in claim 1, wherein the substance is injected into the adventitia.

3. A method as in claim 1, wherein the substance comprises a lipophilic agent selected from the group consisting of anti-neoplastic agents, antiproliferative agents, immunosuppressive agents, anti-inflammatory agents, macrolide antibiotics, antibiotics, antifungals, antivirals, antibodies, lipid lowering treatments, gene therapy agents, anti-sense drugs, metalloproteinase inhibitors, growth factor inhibitors, cell cycle inhibitors, angiogenesis drugs, anti-angiogenesis drugs, and radio-opaque contrast media.

4. A method as in claim 1, wherein the scaffold comprises an expandable frame component having a surface which is at least partly covered by a liquid absorptive structure.

5. A method as in claim 4, wherein the absorptive structure comprises a material selected from the group consisting of a hydrophilic polymer, a hydrophobic polymer, a porous ceramic, and a phosphorylcholine.

6. A method as in claim 4, wherein the absorptive structure comprises a reservoir covered by a porous membrane.

7. A method as in claim 1, wherein the blood vessel is a coronary artery.

\* \* \* \* \*